United States Patent
Aghamohammadi (10) Patent No.: US 10,039,672 B2
(45) Date of Patent: Aug. 7, 2018

(54) VIBRO-ELECTRO TACTILE ULTRASOUND HEARING DEVICE

(76) Inventor: Ali Mohammad Aghamohammadi, Bakersfield, CA (US)

( * ) Notice: Subject to any disclaimer, the term of this patent is extended or adjusted under 35 U.S.C. 154(b) by 308 days.

(21) Appl. No.: 13/407,747

(22) Filed: Feb. 28, 2012

(65) Prior Publication Data

US 2012/0245406 A1 Sep. 27, 2012

Related U.S. Application Data

(60) Provisional application No. 61/466,868, filed on Mar. 23, 2011.

(51) Int. Cl.
- *H04R 25/00* (2006.01)
- *A61F 11/04* (2006.01)
- *A61N 1/04* (2006.01)

(52) U.S. Cl.
CPC ............ *A61F 11/045* (2013.01); *A61F 11/04* (2013.01); *H04R 25/606* (2013.01); *A61N 1/0484* (2013.01); *H04R 2460/13* (2013.01)

(58) Field of Classification Search
CPC ...... A61F 11/04; A61F 11/045; H04R 25/606; H04R 2460/13; A61N 1/0484
USPC ........ 600/25; 381/312; 607/55–57, 136–137, 607/139; 340/407.1
See application file for complete search history.

(56) References Cited

U.S. PATENT DOCUMENTS

| | | | | |
|---|---|---|---|---|
| 4,052,572 A | * | 10/1977 | Schafer | H04R 25/606 381/315 |
| 4,139,742 A | * | 2/1979 | Walker | A61F 11/045 381/323 |
| 4,612,915 A | * | 9/1986 | Hough | H04R 25/606 381/326 |
| 4,982,434 A | | 1/1991 | Lenhardt et al. | |
| 6,466,911 B1 | * | 10/2002 | Cowan et al. | 704/271 |
| 6,731,769 B1 | | 5/2004 | Lenhardt | |
| 7,269,452 B2 | * | 9/2007 | Cheung et al. | 455/575.6 |
| 7,945,064 B2 | | 5/2011 | O'Brien, Jr. et al. | |
| 2004/0202339 A1 | * | 10/2004 | O'Brien et al. | 381/312 |
| 2010/0030012 A1 | | 2/2010 | Meskens | |
| 2010/0040249 A1 | * | 2/2010 | Lenhardt | H04R 25/502 381/316 |
| 2010/0048983 A1 | | 2/2010 | Ball | |
| 2010/0150356 A1 | * | 6/2010 | Uzuanis | H04R 25/70 381/23.1 |
| 2011/0224481 A1 | | 9/2011 | Lee et al. | |

OTHER PUBLICATIONS

Definition of Simultaneous. Printed from WWW on Mar. 17, 2017.*
Definition of Synchronous. Printed from WWW on Mar. 17, 2017.*

* cited by examiner

*Primary Examiner* — Samuel Gilbert
(74) *Attorney, Agent, or Firm* — MU P.C.

(57) ABSTRACT

The present application takes advantage of a simultaneous three pronged approach that converts sound to electricity and subsequently to vibration and ultrasound. The vibrations and electricity are transmitted via skin nerves to the brain to give the deaf or hard of hearing person "hearing sensation" through conditional reflex. The ultrasound wave is transmitted wirelessly to skull and then via bone conduction to the brain and inner ear. This hearing device is not solely dependent on the partially or totally damaged or absent inner ear.

13 Claims, 4 Drawing Sheets

VIBRO-ELECTRO TACTILE ULTRASOUND HEARING DEVICE

BACKGROUND OF THE INVENTION

Field of the Invention

The present invention is directed generally to hearing aid devices.

Description of the Related Art

A typical hearing aid amplifies or modulates sound for a user. However, these devices are not effective for all types of hearing impairments. Other types of hearing aids transfer audible frequency sound vibration to the user that the brain perceives as sound. For example, a Bone-Anchored Hearing Aid ("BAHA") works through direct bone conduction. By way of another example, a cochlear implant converts sound to electrical energy that is transmitted via wires to nerve endings of a Cochlear nerve inside the cochlea of the inner ear. Major and sophisticated surgery is used to install these wires. Tactile and Ultrasonic hearing devices have their own limitation. Unfortunately, each of these approaches has shortcomings such that no one device is capable of enabling every hearing-impaired person to hear. In other words, some types of hearing aids work for some people but not for others. Therefore, a need exists for new hearing devices. A hearing device that overcomes the shortcomings and limitations of hearing devices is particularly desirable.

The present application takes advantage of a simultaneous three pronged converting sound to electricity and subsequently to vibration and ultrasound.

The vibrations and electricity are transmitted via skin nerves to the brain to give the deaf or hard of hearing person "hearing sensation" through conditional reflex. The ultrasound wave is transmitted wirelessly to skull and then via bone conduction to the brain and inner ear. This hearing device is not solely dependent on the partially or totally damaged or absent inner ear. This application with its three combination is a new invention.

The present application provides these and other advantages as will be apparent from the following detailed description and accompanying figures.

DETAILED DESCRIPTION OF THE INVENTION

All publications herein are incorporated by reference to the same extent as if each individual publication or patent application was specifically and individually indicated to be incorporated by reference. Wherever possible, PubMed Identification ("PMID") has been provided for the publications mentioned below. The following description includes information that may be useful in understanding the present invention. It is not an admission that any of the information provided herein is prior art or relevant to the presently claimed invention, or that any publication specifically or implicitly referenced is prior art.

Figure 1:
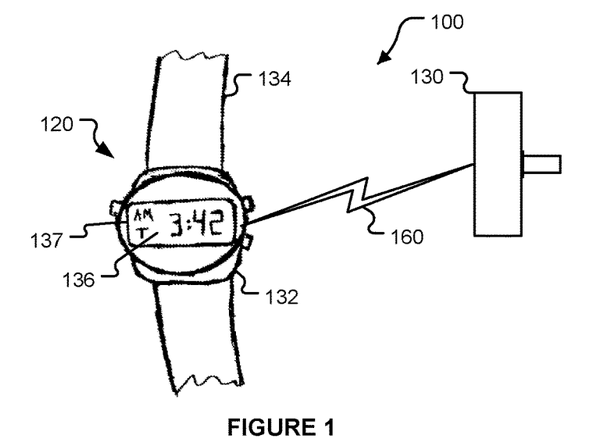
FIG. 1 is a diagram of a system including a transducer assembly and an implantable device.

FIG. 1 illustrates a system 100 implementing a hearing aid or hearing device. The system 100 and system 200 may be described using the noun "Neushan" (spelled "Neushan"), which is an ancient Persian word for a device configured to make one "hear and understand." Further, the system 100 may be described using the verb "Neushidan," which means hearing and understanding.

The system 100 includes a portable transducer assembly 120 and an implantable device 130. The system 100 generates Three different types of signals, an electrical signal, vibration and ultrasound signals, which as explained in detail below, are perceived by the auditory cortex and other parts of a user's brain as sound. The system 100 provides sound information in the form of these [three] different types of vibrations and the electrical signal allowing even profoundly deaf people to perceive sound.

A first of the two different types of vibration and the electrical signal are delivered to the surface of the user's skin. Vibration stimulation applied to the skin is typically referred to as vibrotactile stimulation and electrical stimulation applied to the skin is typically referred to as electrotactile stimulation. Thus, the system 100 delivers both vibrotactile and electrotactile stimulation to the user. Nerves in the skin conduct the vibrotactile and electrotactile stimulation to the brain whereat the auditory cortex [and other parts of the brain] interpret[s] the vibrations and the electrical signal as sound [or auditory sensation; PMID 19726653]. A third of the three different types of vibration is an ultrasonic inertial vibration delivered to a bone (e.g., the mastoid bone) of the user's skull. The skull bone conducts vibrations of the third type to the user's inner ear, which conducts the vibrations to the user's auditory cortex and is perceived as sound.

Figure 2:
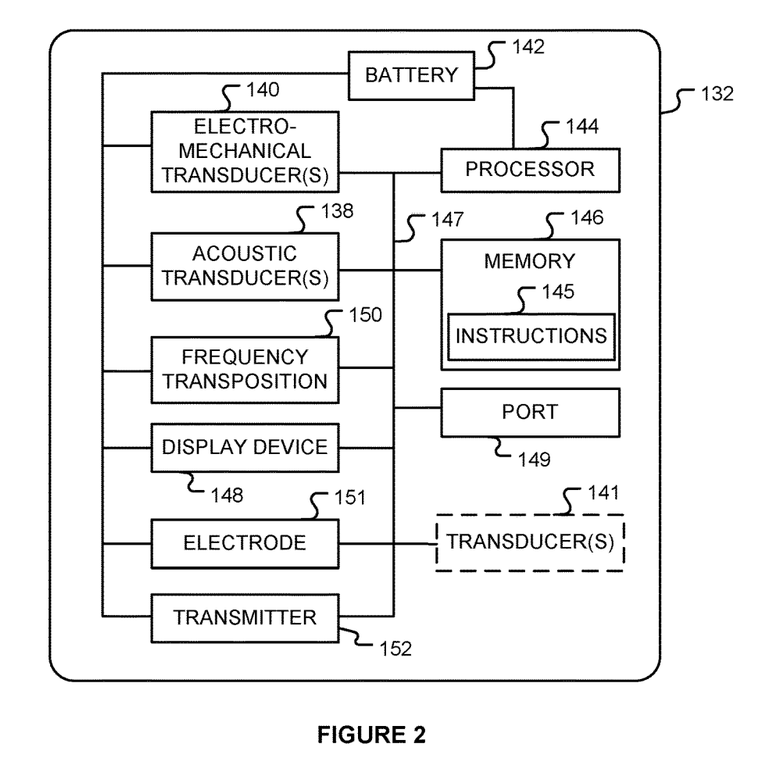
FIG. 2 is a block diagram illustrating one or more acoustic transducers, one or more electro-mechanical transducers, a frequency transposition device, and transmitter housed inside a device housing of the transducer assembly of the system of FIG. 1.

The portable transducer assembly 120 may be wearable by a user. In the embodiment illustrated, the transducer assembly 120 has a device housing 132 attached to a strap 134 and is configured to be worn on the user's wrist like a conventional wristwatch. Optionally, the transducer assembly 120 may include a clock 136 and/or other devices typically worn on a user's wrist. By way of another non-limiting example, the device housing 132 may be attached to a cord or chain (not shown) and worn about the user's neck like a necklace. Further, the device housing 132 may be incorporated in other types of accessories worn or carried by a user, such as an arm band, and the like. FIG. 2 illustrates a portion of the components housed inside the device housing 132. As illustrated in FIG. 2, the transducer assembly 120 includes one or more acoustic transducers 138, one or more electro-mechanical transducers 140, a frequency transposition device 150, one or more electrodes 151, and a transmitter 152. The one or more acoustic transducers 138, the one or more electro-mechanical transducers 140, the frequency transposition device 150, and/or the transmitter 152 may be powered by one or more batteries 142.

The one or more acoustic transducers 138 (e.g., microphones) are each configured to detect sound waves within an audible range of about 20 Hz to about 20 kHz (see FIG. 3), and generate an electrical signal encoding the sounds detected. The one or more acoustic transducers 138 may include a single acoustic transducer that generates an electrical signal encoding the sounds detected and transfers the electrical signal to the electro-mechanical transducer(s) 140, the frequency transposition device 150, and the electrode(s) 151. On the other hand, the one or more acoustic transducers 138 may include one or more separate acoustic transducers for each of the electro-mechanical transducer(s) 140, the electrode(s) 151, and the frequency transposition device 150. By way of another non-limiting example, the one or more acoustic transducers 138 may include one or more acoustic transducers for the frequency transposition device 150 and one or more different acoustic transducers shared by the electro-mechanical transducer(s) 140 and the electrode(s) 151.

Referring to FIG. 2, the one or more electro-mechanical transducers 140 are configured to convert the electrical signal encoding the sounds detected by the one or more acoustic transducers 138 into vibrations detected or felt by the user's skin. Thus, the one or more electro-mechanical transducers 140 are configured to generate vibrations based on the electrical signal encoding the sounds detected by the one or more acoustic transducers 138. The one or more electro-mechanical transducers 140 may be configured to vibrate at least a portion of the device housing 132. Then, the vibrating portion of the device housing 132 may transfer vibrations to the user's skin. Depending upon the implementation details, the one or more electro-mechanical transducers 140 may be small, lightweight, and require low power consumption. Each of the one or more electro-mechanical transducers 140 may include a vibratory member (not shown) constructed from a piezoelectric, high-polymer material coated with an electrically conductive material on both sides. The one or more electro-mechanical transducers 140 may be constructed using any electro-mechanical transducer suitable for use in a conventional vibrotactile hearing device know in the art.

Referring to FIG. 2, the one or more electrodes 151 are in direct contact with the user's skin and are configured to conduct the electrical signal encoding the sounds detected by the one or more acoustic transducers 138 directly to the user's skin. For example, the one or more electrodes 151 may extend through the device housing 132 to contact the user's skin. By way of another non-limiting example, the one or more electrodes 151 may include an electrically conductive portion of the device housing 132 that is in direct contact with the user's skin. For example, the device housing 132 may have a metal back portion in direct contact with the user's skin. The one or more electrodes 151 may include a portion that conducts the electrical signal (encoding the sounds detected by the one or more acoustic transducers 138) to the metal back portion, which in turn conducts the electrical signal to the user's skin.

Figure 3:
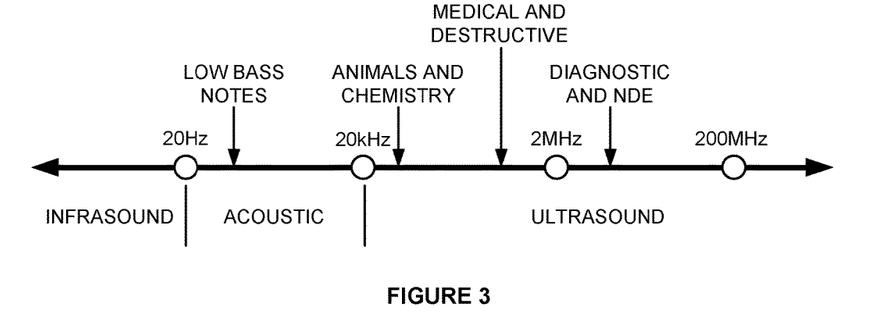
FIG. 3 is an illustration of a frequency spectrum including infrasound, acoustic sound, and ultrasound frequencies.

The frequency transposition device 150 is configured to receive the electrical signal from the one or more acoustic transducers 138 and convert the sound encoded in the electrical signal, which has frequencies within the audible range (e.g., about 20 Hz to about 20 kHz), to an electrical signal encoding ultrasonic sound. Referring to FIG. 3, ultrasound is cyclic sound pressure with a frequency greater than the upper limit of human hearing. Although this limit varies from person to person, it is approximately 20 kHz in healthy, young adults. Thus, 20 kHz may be considered a useful lower limit in describing ultrasound. Ultrasonic noise is defined as broadband noise containing high audible and low ultrasonic frequencies (from 10 kHz to 40 kHz). The upper frequency limit in humans (approximately 20 kHz) is due to limitations of the middle ear, which acts as a low-pass filter. Thus, the ultrasonic sound may include frequencies greater than a lower threshold value (e.g., about 20 kHz). However, as will be explained below, humans can hear ultrasonic sound if the ultrasonic sound is applied directly to a skull bone (e.g., the mastoid bone) and conducted by bones of the skull (via a process referred to as bond conduction) to the cochlea without passing through the middle ear.

Returning to FIG. 2, the frequency transposition device 150 is configured to receive the electric signals, encodes the sound detected by the one or more acoustic transducers 138 and converts the sound from the audible frequency range to the ultrasonic frequency range to produce an electrical signal encoding ultrasonic sound. In the embodiment illustrated, the frequency transposition device 150 is connected to the transmitter 152 (e.g., a radio), which is configured to transmit the electric signal encoding the ultrasonic sound to the implantable device 130 (see FIG. 1). Returning to FIG. 1, the transmitter 152 (see FIG. 2) transmits the electrical signal encoding the ultrasonic sound via a wireless connection 160 to the implantable device 130.

While not illustrated, as is apparent to those of ordinary skill in the art, depending upon the implementation details, the transducer assembly 120 may include additional electrical components such as an analog to digital converter for converting an analog electrical signal generated by the one or more acoustic transducers 138 into a digital electrical signal, and a digital to analog converter for converting the digital electrical signal to an analog electrical signal to be delivered to the electro-mechanical transducer(s) 140 and/or electrode(s) 151. Depending upon the implementation details, the digital electrical signal generated by the analog to digital converter may be received and processed by the frequency transposition device 150.

Optionally, the transducer assembly 120 may be configured to be programmable. In such embodiments, the transducer assembly 120 includes a processor 144 configured to execute instructions 145 stored in a system memory 146. A system bus 147 operatively couples various system components, including the system memory 146, to the processor 144. There may be only one or there may be more than one processor 144, such that the processor 144 of the transducer assembly 120 includes a single central-processing unit (CPU), or a plurality of processing units, commonly referred to as a parallel processing environment. The system bus 147 may be any of several types of bus structures including a memory bus or memory controller, a peripheral bus, and a local bus using any of a variety of bus architectures. A display unit 148 (illustrated as the LCD display 137 in FIG. 1) or other type of display device may be connected to the system bus 147 via an interface, such as a video adapter (not shown).

The memory 146 may include memory local to the transducer assembly 120 as well as removable memory, such as a flash memory device, and the like. The system memory 146 may also be referred to as simply the memory, and includes read only memory (ROM) and random access memory (RAM). A basic input/output system (BIOS) may be stored in ROM. The BIOS contains the basic routines that help to transfer information between elements within the transducer assembly 120, such as during start-up. The memory 146 may include a hard disk drive for reading from and writing to a hard disk. The memory 146 may include solid-state memory (such as flash memory) of the type typically used in small portable devices.

The memory 146 may also include a drive, a communication interface, and/or a port 149, such as a network port, USB port, a flash memory slot, and the like for reading from and/or writing to removable or portable media, such as, a flash memory device. The port 149 may be used to connect the transducer assembly 120 to another computing device. The port 149 may be used to transfer information (such as processor-executable instructions, data, and the like) from the memory 146, transfer information (such as processor-executable instructions, data, and the like) to the memory 146, and the like. For example, the port 149 may be used to transfer information to and/or from portable memory (e.g., a flash drive). Alternatively, the port 149 may be coupled to a network (e.g., the Internet) and used to transfer information to and/or from a remote computing device (e.g., a personal computer, etc.) over the network.

The memory 146 provides nonvolatile storage for the processor-readable instructions 145, data structures, program modules, and other data for the transducer assembly 120. A number of program modules may be stored in the memory 146, including an operating system, one or more application programs, other program modules, and program data.

The instructions 145 stored in the memory 146 include instructions that instruct the processor 144 to issue commands to the electro-mechanical transducer(s) 140, the one or more acoustic transducers 138, the frequency transposition device 150, the transmitter 152, and/or the display device 148. By way of a non-limiting example, the processor 144 may receive the electric signal generated by the acoustic transducer(s) 138. In embodiments in which the acoustic transducer(s) 138 generate analog electrical signals, an analog to digital converter may convert the analog electrical signals generated by the acoustic transducer(s) 138 into digital electrical signals for processing by the processor 144. The processor 144 may direct the electro-mechanical transducer(s) 140 to generate vibrations based on the electrical signal. The processor 144 may forward the electric signal to the electrodes(s) 151. Optionally, the processor 144 may process the electrical signal before forwarding it to the electrodes(s) 151 and/or the electro-mechanical transducer(s) 140. Optionally, the digital electrical signal may be converted to an analog signal by a digital to analog converter before the electrical signal is received by the electrodes(s) 151 and/or the electro-mechanical transducer(s) 140. The processor 144 may also direct the frequency transposition device 150 to convert the frequencies of the sound encoded in the electrical signal to the ultrasound frequency range. Next, the processor 144 may direct the transmitter 152 to transmit an electrical signal encoding the ultrasonic sound to the implantable device 130 via the wireless connection 160. The instructions 145 may include instructions for encoding the electrical signal for transmission by the transmitter 152. The instructions 145 may also include instructions for directing the processor 144 to establish the wireless connection 160 with the implantable device 130. Optionally, the frequency transposition device 150 may be implemented as hardware, software (e.g., instructions executed by the processor 144), or a combination thereof.

Returning to FIG. 1, the implantable device 130 is configured to receive the electric signal encoding the ultrasonic sound transmitted by the transmitter 152 (see FIG. 2) via the wireless connection 160, generate ultrasonic inertial vibrations based on the electric signal received, and deliver those ultrasonic inertial vibrations to a skull bone (e.g., the cortex of the mastoid bone). In the embodiment illustrated in FIGS. 4-6, the implantable device 130 includes an external unit 170 and an anchor portion 172. The external unit 170 has a housing 171 that is selectively attachable and detachable from the anchor portion 172.

Figure 6:
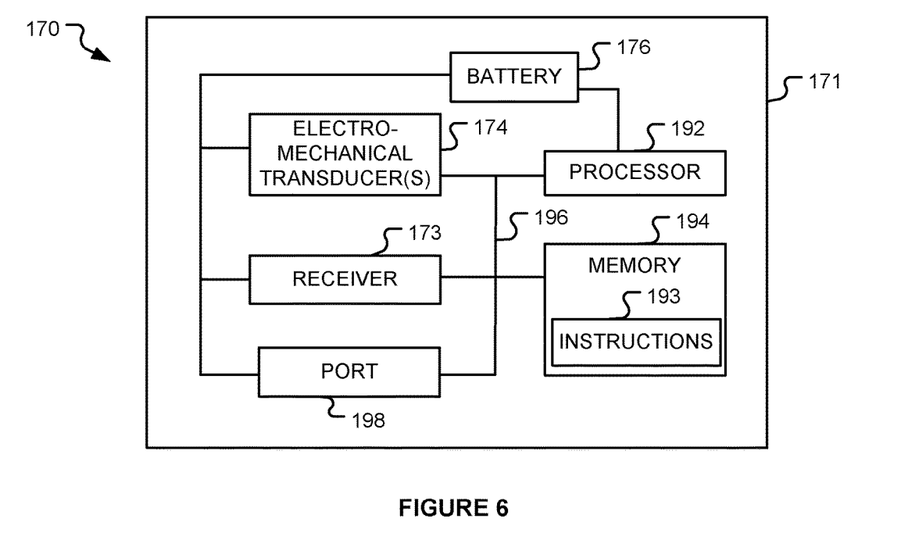
FIG. 6 is a block diagram illustrating one or more electro-mechanical transducers, and a receiver housed inside a device housing of the external unit of the implantable device of FIG. 1.

Turning to FIG. 6, the housing 171 at least partially houses a receiver 173 and one or more electro-mechanical transducers 174. The housing 171 may be relatively small (e.g., having the size of a conventional behind-the-ear hearing aid). One or more batteries 176 may power the receiver 173 and/or one or more electro-mechanical transducers 174. Depending upon the implementation details, the one or more batteries 176 may be configured to power the receiver 173 and/or one or more electro-mechanical transducers 174 for about six days to about fourteen days.

The receiver 173 is configured to receive the electric signal encoding the ultrasonic sound transmitted by the transmitter 152 (see FIG. 2) of the transducer assembly 120 (see FIG. 1). The one or more electro-mechanical transducers 174 are each configured to convert the electric signal received to ultrasonic inertial vibrations.

While not illustrated, as is apparent to those of ordinary skill in the art, depending upon the implementation details, the external unit 170 may include additional electrical components such as a digital to analog converter for converting a digital electrical signal received by the receiver 173 to an analog electrical signal to be delivered to the one or more electro-mechanical transducers 174.

Figure 4:
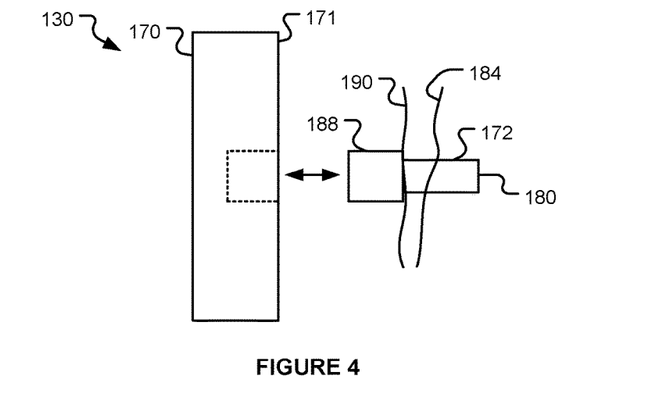
FIG. 4 is an illustration of the implantable device of the system of FIG. 1 including an external unit that is detached from an anchor portion.
Figure 5:
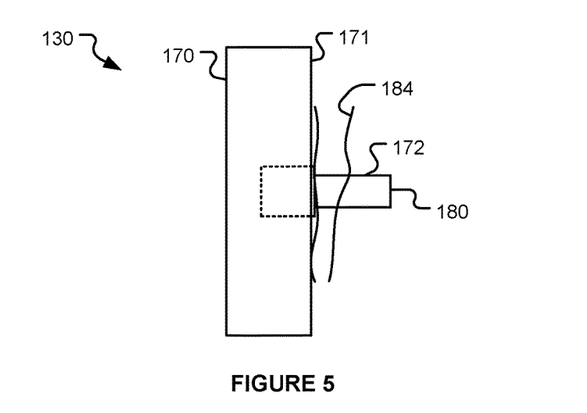
FIG. 5 is an illustration of the implantable device with the external unit attached to the anchor portion.

The anchor portion 172 has a first end portion 180 configured to be implanted in a skull bone 184 (e.g., the cortex of the mastoid bone). By way of a non-limiting example, the anchor portion 172 may be implanted in the skull bone 184 under local anesthesia. Opposite the first end portion 180, the anchor portion 172 has an external second end portion 188 positioned external to the user's skin 190 when the first end portion 180 is implanted in the skull bone 184. The external second end portion 188 is configured to be selectively coupled to and uncoupled from the housing 171. The anchor portion 172 may be implemented using the titanium implant or rod of a conventional BAHA, which is typically only about 3 mm thick.

The implanted first end portion 180 bonds with the surrounding tissue in a process referred to as osseointegration. The housing 171 can be connected or attached to the external second end portion 188 of the anchor portion 172 for use after osseointegration is complete, which is typically about two months to about six months after implantation.

The housing 171 may be coupled to the external second end portion 188 of the anchor portion 172 by a magnet (not shown) or other type of connector. By way of a non-limiting example, the housing 171 may be connected to the external second end portion 188 of the anchor portion 172 via a releasable snap-lock coupling (not shown) configured to releasably clip the housing 171 to the external second end portion 188. As mentioned above, the receiver 173 and/or one or more electro-mechanical transducers 174 may be powered by the one or more batteries 176. As illustrated in FIG. 4, the housing 171 may be detached from the anchor portion 172 so that the one or more batteries 176 may be replaced when they have been depleted. Further, after being detached, as illustrated in FIG. 4, the housing 171 may be reattached to the anchor portion 172. As a safety feature, the snap-lock coupling may be configured to detach upon impact to prevent damage to the anchor portion 172 or surrounding tissues.

The implantable device 130 is configured for use in FIG. 5. In this configuration, the one or more electro-mechanical transducers 174 are positioned to vibrate the second end portion 188 of the anchor portion 172. When vibrated by the one or more electro-mechanical transducers 174, the anchor portion 172 transmits ultrasonic inertial vibrations by direct conduction through bone to the inner ear, bypassing the external auditory canal and middle ear. The vibrating skull and inner ear stimulate nerve fibers of the inner ear, enabling the user to hear the sound detected by the one or more acoustic transducers 138 (see FIG. 2) of the transducer assembly 120 (see FIG. 1). See e.g., Nakagawa, S. et al., *Can ultrasonic hearing aids be developed?*, Proceedings of the Symposium on Biological and Physiological Engineering, Vol. 15., pp. 329-332 (2000); and Kagomiya, T. and Nakagawa, S., *An Evaluation of Bone-conducted Ultrasonic Hearing Aid regarding Perception of Paralinguistic Information*, Proceedings of Speech Prosody 100867:1-4 (2010).

Optionally, the external unit 170 may be configured to be programmable. In such embodiments, the external unit 170 includes a processor 192 configured to execute instructions 193 stored in a system memory 194. A system bus 196 operatively couples various system components, including the system memory 194, to the processor 192. The external unit 170 may also include a port 198. The processor 192 may be constructed using any processor(s) described above as suitable for constructing the processor 144 (see FIG. 2) of the transducer assembly 120 (see FIG. 1). The system bus 196 may be constructed using any bus architectures described above as suitable for constructing the system bus 147 (see FIG. 2) of the transducer assembly 120 (see FIG. 1). The memory 194 may be constructed using any memory devices described above as suitable for constructing the memory 146 (see FIG. 2) of the transducer assembly 120 (see FIG. 1). The port 198 may be constructed using any devices described above as suitable for constructing the port 149 (see FIG. 2) of the transducer assembly 120 (see FIG. 1).

The port 198 may be used to connect the external unit 170 to another computing device. The external unit 170 may be used to transfer information (such as processor-executable instructions, data, and the like) from the memory 194, transfer information (such as processor-executable instructions, data, and the like) to the memory 194, and the like. For example, the port 194 may be used to transfer information to and/or from portable memory (e.g., a flash drive). Alternatively, the port 194 may be coupled to a network (e.g., the Internet) and used to transfer information to and/or from a remote computing device (e.g., a personal computer, etc.) over the network.

The memory 194 provides nonvolatile storage for the processor-readable instructions 193, data structures, program modules, and other data for the external unit 170. A number of program modules may be stored in the memory 194, including an operating system, one or more application programs, other program modules, and program data.

The instructions 193 stored in the memory 194 may include instructions that instruct the processor 192 to issue commands to the electro-mechanical transducer(s) 174 and/or the receiver 173. By way of a non-limiting example, the processor 192 may receive the electric signal transmitted by the transmitter 152 (see FIG. 2) from the receiver 173. Then, the processor 192 may direct the electro-mechanical transducer(s) 174 to generate ultrasonic inertial vibrations based on the electrical signal. Optionally, the processor 192 may process the electrical signal before delivering it to the electro-mechanical transducer(s) 174. For example, the instructions 193 may include instructions for decoding the ultrasonic sound encoded in the electrical signal received by the receiver 173. An optional digital to analog converter may convert the electrical signal received from the processor 192 to an analog electrical signal before the electrical signal is delivered to the electro-mechanical transducer(s) 174. The instructions 193 may also include instructions for directing the processor 192 to establish the wireless connection 160 with the transducer assembly 120.

The transmitter 152 (see FIG. 2) of the transducer assembly 120 (see FIG. 1) may be configured to communicate with the receiver 173 using the [wireless] communication standard. However, other wireless communication protocols and/or standards may be used and the system 100 is not limited to the Bluetooth communication standard.

Figure 7:
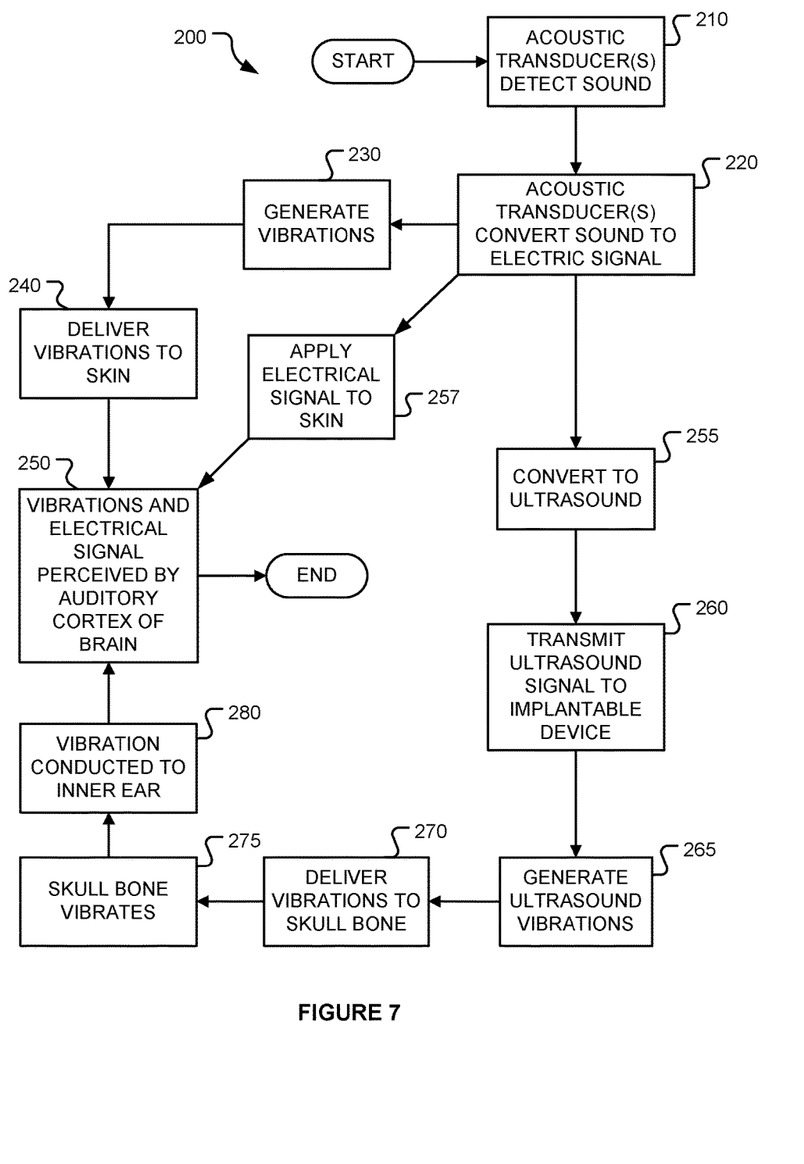
FIG. 7 is a flow diagram of a method at least partially performable by the system of FIG. 1.

FIG. 7 is a flow diagram of a method 200 at least partially performable by the system 100. The method will be described with respect to FIGS. 2 and 7. In first block 210, the one or more acoustic transducers 138 detect sounds. In next block 220, the one or more acoustic transducers 138 convert the sounds detected into one or more electrical signals encoding the sounds detected. Then, the method 200 branches into a first, second, and third branch, with the branches being perform simultaneously.

With respect to the first branch, in block 230, the one or more electro-mechanical transducers 140 generate vibrations based on the electrical signal(s). In block 240, the vibrations are delivered to the user's skin. Then, in block 250, the vibrations are perceived as sound by the auditory cortex of the user's brain.

With respect to the second branch, in block 257, the one or more electrodes 151 deliver the electrical signal(s) to the user's skin. Then, in block 250, the electrical signal(s) are perceived as sound by the auditory cortex of the user's brain.

With respect to the third branch, in block 255, the frequency transposition device 150 modifies (or transposes) the frequencies of the sounds encoded in the electrical signal(s) such that the frequencies of the sounds are in the ultrasound frequency range. For example, the frequency transposition device 150 may shift the frequencies of the sounds into the ultrasound frequency range. In block 260, the transmitter 152 of the transducer assembly 120 transmits the electrical signal(s) encoding the sounds in the ultrasound frequency range to the receiver 173 (see FIG. 6) of the implantable device 130 (see FIGS. 1, 4, and 5).

Turning to FIGS. 6 and 7, in block 265, the one or more electro-mechanical transducers 174 of the external unit 170 of the implantable device 130 (see FIGS. 1, 4, and 5) generate ultrasonic inertial vibrations based on the signal received by the receiver 173.

In block 270, the vibrations generated in block 265 are delivered to a bone of the user's skull causing the skull bone to vibrate in block 275.

In block 280, the vibration induced in the skull bone is conducted to other skull bones, including the Petrus bone, and eventually reaches the user's inner ear.

Then, in block 250, the ultrasonic inertial vibrations are perceived as sound by the auditory cortex of the user's brain.

Then, the method 200 terminates.

Returning to FIG. 2, in an alternate embodiment, one or more transducers 141 are connected to the frequency transposition device 150 and the transmitter 152. The one or more transducers 141 are configured to receive the electrical signal encoding ultrasonic sound from the frequency transposition device 150, convert the electric signal into ultrasonic inertial vibrations, and provide the ultrasonic inertial vibrations to the transmitter 152 for transmission thereby to the implantable device 130. In such an alternate embodiment, the transmitter 152 is configured to transmit the ultrasonic inertial vibrations (instead of the electrical signal encoding the ultrasonic sound) to the implantable device 130 (see FIG. 1), and the receiver 173 (see FIG. 6) is configured to receive the ultrasonic inertial vibrations transmitted by the transmitter 152. In such an alternate embodiment, the one or more electro-mechanical transducers 174 (see FIG. 6) are omitted from the external unit 170 (see FIG. 6). Instead, the ultrasonic inertial vibrations are received by the receiver 173, and may be delivered directly to the anchor portion 172. Optionally, in embodiments including the processor 192, the processor 192 may process the ultrasonic inertial vibrations before they are delivered to the anchor portion 172.

The method 200 may be performed by the alternate embodiment of the system 100. For example, the first and second branches of the method 200 are performed by the alternate embodiment of the system 100 in the same manner described above. Turning to the third branch, in block 255, the frequency transposition device 150 modifies (or transposes) the frequencies of the sounds encoded in the electrical signal(s) such that the frequencies of the sounds are in the ultrasound frequency range. Then, the one or more transducers 141 receive the electrical signal encoding ultrasonic sound from the frequency transposition device 150, convert the electric signal into ultrasonic inertial vibrations, and provide the ultrasonic inertial vibrations to the transmitter 152. In block 260, the transmitter 152 of the alternate embodiment transmits the ultrasonic inertial vibrations (instead of the electrical signal(s) encoding the sounds in the ultrasound frequency range) to the receiver 173 (see FIG. 6) of the implantable device 130 (see FIGS. 1, 4, and 5). As mentioned above, the one or more electro-mechanical transducers 174 are omitted from the external unit 170 in the alternate embodiment. In block 265, the ultrasonic inertial vibrations are received by the receiver 173. In block 270, the ultrasonic inertial vibrations received in block 265 are delivered to a bone of the user's skull causing the skull bone to vibrate in block 275. In block 280, the vibration induced in the skull bone is conducted to other skull bones, including the petrus bone, and eventually reaches the user's inner ear. Then, in block 250, the ultrasonic inertial vibrations are perceived as sound by the auditory cortex of the user's brain.

Returning to FIG. 1, by providing two different types of vibrations and an electrical signal (electrotactile stimulation) to the user, the system 100 combines both ultrasonic hearing and tactile hearing (using both vibrotactile and electrotactile stimulation). As discussed above, each of these types of hearing has its limitations or deficiencies. However, by combining these two approaches, the system 100 compensates for the respective deficiencies of tactile and ultrasonic hearing. In other words, the components that enable tactile hearing (e.g., the one or more electro-mechanical transducers 140, and the one or more electrodes 151) and the components that enable ultrasonic hearing (e.g., the frequency transposition device 150, and the implantable device 130) complement one another. Thus, the system 100 provides superior performance to devices configured to provide only tactile hearing or ultrasonic hearing.

The system 100 allows the user to perceive sound via conditional reflexes trigged by electrical and vibratory stimulation of skin, and stimulation of the ultrasonic receptors of the inner ear and central neural hearing pathway. These cues are presented to the auditory cortex [and other parts] of the brain for interpretation thereby. The system 100 provides a [much] less invasive alternative to a cochlear implant, which requires surgical implantation and carries a set of undesirable complications. In particular, a cochlear implant infringes upon the protective mechanisms of the brain because the cochlear implant's electrodes must stimulate the cochlear nerve in the scala tympani of the inner ear. This exposes the brain to the middle ear, which increases the risk of infection and exposure to environmental hazards. The system 100 may be used without such a sophisticated surgery. By way of a non-limiting example and as mentioned above, the anchor portion 172 of the implantable device 130 may be implanted into the cortex of the mastoid bone under local anesthesia. The system 100 may also be used by people having unilateral hearing loss and is suitable for people who cannot use conventional hearing aides.

RELATED MEDICAL LITERATURE

I—Ultrasonic Hearing

As mentioned above, ultrasonic hearing can occur when ultrasound is applied directly into a skull bone of a subject and reaches the subject's cochlea through bone conduction without passing through the subject's middle ear. Although, the mechanism that allows humans to perceive ultrasonic stimuli is not well known or understood, there are two leading hypotheses relating to how ultrasonic perception of sound may occur. The first theory involves a hair cell region at the base of the cochlea that is believed to be capable of interpreting ultrasonic signals. The second theory involves the vestibular and saccular regions that may also be capable of responding to ultrasonic stimuli. Unfortunately, the anatomy of the ear (the tympanic membrane and ossicles) is unable to deliver acoustic ultrasonic energy, perceived in the environment, to either the cochlear or vestibular regions because of the impedance mismatch of the tympanic membrane. See Abramovich, S. J., *Auditory Perception of Ultrasound in Patients with Sensorineural Hearing Loss and Conductive Hearing Loss*, Journal of Laryngology, Otology, Vol. 92(10), pages 861-867, PMID 712218 (October 1978).

Ultrasonic vibrations can be perceived as audible sounds when a piezoelectric transducer is pressed against certain areas of the human body. In the range of frequencies investigated (20 to 108 kcy/sec), the threshold of perception seemed to lie near the threshold of feeling (about 10(−4) watt/cm(2)), and the perceived audible sound appeared to be between 8 and 9 kcy/sec, as judged by test subjects. The threshold of perception and the perceived frequency appear to be dependent upon the hearing characteristics of the individual. See Haeff, A. and Knox, C., *Perception of ultrasound*, Science, Vol. 139, no. 3555, pp. 590-592, PMID 17788293 (Feb. 15, 1963).

Hearing sensations induced by ultrasound in the frequency range 20-80 kcps are determinable with the Electrical Response Audiometry ("ERA"). The latency periods of the evoked potentials occurred is amounted between 100 and 300 msec. No difference has been found between ultrasound-induced potentials and the potentials evoked by usual tonal stimuli. See Flach, M., Hofmann, G., Ertel, H., and Knothe, J. [*Measurements of hearing sensations in ultrasound range by electrical response audiometry (ERA) (author's transl)*], Laryngol Rhinol Otol (Stuttg), 57(7), pp. 680-6, PMID 682786 (July 1978).

Early acoustic evoked potentials (brain stem evoked response) may be received by bone conduction after ultrasound irritation (40 kHz). In comparison with the brain stem potential, which is received by the some bone conduction by 4 kHz, there are differences in the pattern of the potential and in the latency shift. It may be thought of a retro-cochleare perception of the ultrasound because of the 1 msec earlier potential. See Floch, M., Hoffman, G. Ultrasound hearing by humans. Objectivation with brain stem potentials [Article in German (Authors Translation)], Laryngol Rhinol Otol (Stuttg) 59(12), pp 840-3, PMID 7278474 (1980).

The attenuation of bone-conducted stimuli across the human skull was determined in audiometric, ultrasonic, and supersonic frequency ranges (250 to 64,000 Hz). An increase in attenuation with an increase in frequency, as well as significant resonance effects, has been observed. For the audiometric frequency range, bone conduction stimulation of one side of the head results in almost equal stimulation of the other side. In the ultrasonic and supersonic ranges, the contralateral side is progressively isolated. See Dunlap, S., Lenhardt, M., and Clarke, A., *Human skull vibratory patterns in audiometric and supersonic ranges*, Otolaryngol Head Neck Surg., 99(4), pp. 389-91, PMID 3148888 (October 1988).

Using three-dimensional Positron emission tomography ("PET"), the cortical areas activated by bone-conducted ultrasound were measured from five profoundly deaf subjects and compared with the cortical areas of normal-hearing subjects activated by stimuli through bone-conducted ultrasonic, air-conducted, bone-conducted, and vibro-tactile hearing aids. All of the hearing aids, including the ultrasonic hearing aid, consistently activated the medial portion of the primary auditory cortex of the normal volunteers. The same cortical area was also significantly activated in the profoundly deaf subjects although the percentage increase in regional cerebral blood flow (rCBF) was smaller than in normal subjects. These results suggest that extra-cochlear routes convey information to the primary auditory cortex and can therefore produce detectable sound sensation even in the profoundly deaf subjects, who reported a sensation themselves. See Imaizumi S. et al., *Ultrasound Activates the Auditory Cortex of Profoundly Deaf Subjects*, Neuroreport Vol. 12(3), pages 583-586, PMID: 11234768 (Mar. 5, 2001).

Bone-conducted ultrasonic hearing has been found capable of supporting frequency discrimination and speech detection in normal, older hearing-impaired, and profoundly deaf human subjects. When speech signals were modulated into the ultrasonic range, listening to words resulted in the clear perception of the speech stimuli and not a sense of high-frequency vibration. These data suggest that ultrasonic bone conduction hearing has potential as an alternative communication channel in the rehabilitation of hearing disorders. See Lenhardt, M., Skellet, R., Wang, P., and Clarke, A. *Human Ultrasonic Speech Perception*, Science, 253(5015), pp. 82-5, PMID 2063208 (Jul. 5, 1991).

Human listeners can perceive speech signals in a voice-modulated ultrasonic carrier from a bone-conduction stimulator, even if the listeners are patients with sensorineural hearing loss. The bone conducted ultrasonic hearing aid (BUCHA) shows good performance in transmitting information on the speaker's intention and has the capability of being an effective tool in expressive oral communications. See Takayuchi Kagomiya and Seiji Nakagawa, *An Evaluation of Bone-Conducted Ultrasonic Hearing Aid Regarding Perception of Paralinguistic Information*, Institute for Human Science and Medical Engineering, National Institute of Advanced Industrial Science and technology, (AIST), Japan. A copy of this reference is filed herewith and incorporated herein by reference in its entirely.

A study showed that it is possible to transmit language information using bone-conducted ultrasound (BCU) in normal-hearing subjects. The results suggest the possibility of a difference in speech recognition between BCU and air-conducted audible sound (ACAS). See Yamashita, A. et al., *Comparison between bone-conducted ultrasound and audible sound in speech recognition*, Acta Otolaryngol Suppl., 562, p. 34-9, PMID 19848237 (June 2009).

Nonlinear conduction that demodulates audible signals from ultrasounds provides inputs to the cochlea. See Fujimoto K., et al., *Nonlinear Explanation for Bone-Conducted Ultrasonic Hearing*, Hearing Research, Vol. 204(1-2), PMID 15925206 (June 2005).

The intelligibility of familiar words is higher than that of unfamiliar words. Further, the results of a monosyllable intelligibility test with bone-conducted ultrasound and those of a test with air-conducted sound showed a similar pattern of speech. The increase in the intelligibility of bone-conducted ultrasonic speech did not exceed the increase in the intelligibility of air-conducted speech as the sound level rose. See U.S. Pat. No. 6,217,508, filed on Aug. 14, 1998, and entitled Ultrasonic Hearing System; and Okamoto, Y., Nakagawa, S., Fujimoto, K., and Tonoike, M., *Intelligibility of bone-conducted ultrasonic speech*, Hear Res. 208(1-2), pp. 107-13, PMID 16019175 (October 2005).

Flach, M., and Hofmann, G., [*Ultrasound hearing by humans: objectivation with brain stem potentials (author's transl)*], Laryngol Rhinol Otol (Stuttg), 59(12), pp. 840-3, PMID 7278474 (1980); and Imaizumi, S. et al., *Ultrasound activates the auditory cortex of profoundly deaf subjects*, Neuroreport, 12(3), pp. 583-6, PMID 11234768 (Mar. 5, 2001).

II—Tactile Hearing

Vibrotactile devices convert sound to a vibration that may be felt or detected by a subject's skin. Thus, the subject is able to "hear" sound, i.e. Auditory sensation.

Vibration stimuli, derived from speech or a fixed frequency cause higher widespread activity within auditory cortical regions of brain in deaf people than normal people for both stimulus types. Life-long somatosensory stimulation due to hearing aid use could explain the greater activity observed with deaf participants. See Auer, E., Bernstein, L., Sungkarat, W., and Singh, M., *Vibrotactile Activation of the Auditory Cortices in Deaf versus Hearing Adults*, Neuroreport, 18(7), pp. 645-8, PMID 17426591 (May 7, 2007); Suarez, H. et al., *Vibrotactile Aid and Brain Cortical Activity*, Acta Otolaryngol., 117(2), pp. 208-10, PMID 9105450 (March 1997); and Burton H. et al., *Cortical Network for Vibrotactile Attention: an fMRI Study*, Human Brain Mapping, Vol. 29(2), pages 207-221, PMID 17390318 (February 2008).

The right inferior frontal gyrus ("IFG") and both left and right insula were more activated during identification conditions than during localization in both touch and audition. The reverse dissociation was found for the left and right inferior parietal lobules ("IPL"), the left superior parietal lobule ("SPL") and the right precuneus-SPL, which were all more activated during localization conditions in the two modalities. Vibrotactile stimuli can elicit compelling auditory sensation even when sound energy levels are minimal and undetectable. See Reinier L. A. et al., *Multisensory Integration of Sounds and Vibrotactile Stimuli in Processing Streams for "What" and "Where,"* Journal of Neuroscience, Vol. 29(35), pages 10950-10960, PMID 19726653 (Sep. 2, 2009).

Results for combined vibrotactile and auditory detection indicated that (1) performance improved for synchronous presentation, (2) performance was not affected by the relative phase of the auditory and tactile sinusoidal stimuli, and (3) performance for non-overlapping stimuli improved only if the tactile stimulus preceded the auditory. See Wilson E. C. et al., *Integration of Auditory and Vibrotactile Stimuli: Effects of Phase and Stimulus-Onset Asynchrony*, Journal of the Acoustical Society of America, Vol. 126(4), pages 1960-1974, PMID 19813808 (October 2009). The interaction between vibrotaction and audition does not appear to occur at an early perceptual level. The presence of a vibrotactile stimulus induces an increase in the perceived loudness of the auditory tones. See Yarrow, K., Haggard, P., and Rothwell, J., *Vibrotactile-Auditory Interactions are Post-Perceptual*, Perception, 37(7), pp. 1114-30, PMID 18773733 (2008).

There is good evidence for critical periods in the development of sensory processes (particularly vision and hearing) and language functions. If appropriate experience is absent during these critical periods, later performance is impaired. Early exposure to a tactile transformation of speech (for example) might provide the profoundly deaf with two significant advantages. Firstly, early exposure increases the chance that the cutaneous system will develop neural connections appropriate to the handling of the transformed speech signal. In other words, tactile sensitivity can be optimized. Secondly, early exposure to language as a process associated with the cutaneous system (rather than the auditory system) might favor the development of cortical connections consistent with the sensory substitution system. Such plasticity might no longer exist when the critical period has passed. See Richardson B. L. and Wuillemin, D. B., *Critical Periods for the Transmission of Tactual Information*, International Journal of Rehabilitation Research, Vol. 4(2), pages 175-179, PMID 7275423 (1981). For more information see Blamey, P J., *Speech perception using combinations of auditory, visual, and tactile information*, J Rehabil Res Dev., 26(1), pp. 15-24, PMID 2521904 (Winter 1989).

Tactile aids are well accepted by patients with severe to profound sensorineural hearing loss who do not benefit from conventional hearing aids. One hundred percent of the cases passed the first stage (detection) successfully. In the second stage (beginning pattern perception) all the cases with two and seven channel tactile aids were able to distinguish all kinds of sounds. They could differentiate between speech and non-speech sounds. In the third stage (recognition of speech), all the cases were able to recognize environmental and "sound maker" sounds, but only 43% of the individuals were able to recognize speech sounds and repeat correctly with two-channel tactile aids. In the fourth stage (comprehension of words), identification and repetition of the words were only possible with seven-channel tactile aids. See Karimi-Yazdi, A., et al., *Application and usage of Tactile Aid in Iran*, Archives of Iranian Medicine, Vol. 9(4), pages 344-347, PMID 17061607 (October 2006).

Tactile aids used for the development of improved speech production skills by profoundly deaf children showed large improvements in the post-training tokens. See Plant, G., Horan, M., and Reed, H., *Speech teaching for deaf children in the age of bilingual/bicultural programs: the role of tactile aids*, Scand Audiol Suppl., 47, pp. 19-23, PMID 9428039 (1997). See also Richardson, B., and Frost, B., *Sensory substitution and the design of an artificial ear*, J Psychol., 96(2d Half), pp. 259-85, PMID 886486 (July 1977).

Vibro-tactile aid used by the profoundly deaf adults provided very useful information as to speech and non-speech stimuli with the subjects performing best on those tasks where time/intensity cues provided sufficient information to enable identification. See Plant, G. *Tactile perception by the profoundly deaf. Speech and environmental sounds*, Br J Audiol, 16(4), pp. 233-44, PMID 6897619 (November 1982) Frequency-modulated and amplitude-modulated vibratory stimulation is a good choice in a practical device for the profoundly hearing impaired. To improve information transfer for vibrotactile stimuli, frequency and amplitude modulation should be used together rather than using frequency modulation or amplitude modulation in isolation. See Summers, I. et al., *Vibrotactile and electrotactile perception of time-varying pulse trains*, J Acoust Soc Am., 95(3), pp. 1548-58, PMID 8176058 (March 1994).

Hearing improvement achieved by usage of Nucleus 22-channel cochlear implants; and the two-channel Tactaid II+ vibrotactile aids were compared. Different patterns of speech discrimination are provided by the three sensory prosthetic devices. For all contrasts, mean discrimination performance with the Nucleus device was better than that observed for the other two devices. Interactions between device and speech contrast were not observed. Examination of individual subject performance revealed that each device group had a distribution of good to poor performers. The results suggest that the change/no change procedure is able to provide information regarding speech perception through sensory prosthetic devices despite existing differences in vocabulary and language skills of subjects. See Carney, A. et al., *A comparison of speech discrimination with cochlear implants and tactile aids*, J Acoust Soc Am., 94(4), pp. 2036-49, PMID 8227746 (October 1993).

The subjects with early onset of deafness who received their single- or multichannel cochlear implant before age ten demonstrated the highest speech intelligibility, whereas subjects who did not receive their device until after age ten had the poorest speech intelligibility. There was no obvious difference in the speech intelligibility scores of these subjects as a function of type of device (implant or tactile aid). On the average, the post-implant or tactile aid speech intelligibility of the subjects with early onset of deafness was similar to that of hearing aid users with hearing levels between 100 and 110 dB HL and limited hearing in the high frequencies. The speech intelligibility of subjects with late onset of deafness showed marked deterioration after the onset of deafness with relatively large improvements by most subjects after they received a single-channel or multichannel implant. See Osberger, M., Maso, M., and Sam, L., *Speech intelligibility of children with cochlear implants, tactile aids, or hearing aides*, J Speech Hear Res., 36(1), pp. 186-203, PMID 8450658 (February 1993).

The vibrotactile aid provided very useful information as to speech and non-speech stimuli with the subjects performing best on those tasks where time/intensity cues provided sufficient information to enable identification.

Three vibrotactile vocoders were compared in a training study involving several different speech perception tasks. Results showed that the three vocoders provided equivalent information in word-initial and word-final tactile-only consonant identification. See Bernstein, L., Demorest, M., Coulter, D., and O'Connell, M., Lipreading sentences with vibrotactile vocoders: performance of normal-hearing and hearing-impaired subjects, J Acoust Soc Am., 90(6), pp. 2971-84, PMID 1838561 (December 1991). See also Ozdamar, O., Lopez, C., Oiler, D., Eilers, R., Miskiel, E., and Lynch, M., *FFT-based digital tactile vocoder system for*

*real-time use*, Med Biol Eng Comput., 30(2), pp. 213-8, PMID 1453787 (March 1992); and Richardson, B., *Separating signal and noise in vibrotactile devices for the deaf.* Br J Audiol., 24(2), pp. 105-9, PMID 2350619 (April 1990).

The type and degree of benefit provided by tactile aids for the hearing-impaired varies from device to device, as a function of such variables as the number of tactile transducers, type of stimulation, location of stimulation, and the nature of processing of the input acoustic waveform. The results of these evaluations suggest that tactile aids, particularly multichannel devices that employ a number of tactile transducers and convey information about the spectral content of the speech signal, can be of significant benefit in speech perception in children and adults. These findings suggest that even a relatively brief period of training with a tactile aid can lead to improvements in speech production by hearing-impaired children. See Weisenberger, J., and Kozma-Spytek, L., *Evaluating tactile aides for speech perception and production by hearing-impaired adults and children*, Am J Otol., 12 Suppl, pp. 188-200, PMID 2069181 (1991); and Blamey, P., Cowan, R., Alcantara, J., and Clark, G., *Phonemic information transmitted by a multichannel electrotactile speech processor*, J Speech Hear Res. 31(4), pp. 620-9, PMID 3230892 (December 1988).

Speech perception studies using a multichannel electrotactile speech processor, residual hearing, and lipreading. Results indicate that the electrotactile aid may be useful for patients with little residual hearing and for the severely to profoundly hearing impaired, who could benefit from the high-frequency information presented through the tactile modality, but unavailable through hearing aids. See Cowan, R., Alcantara, J., Whitford, L., Blarney, P., and Clark, G., *Speech perception studies using a multichannel electrotactile speech processor, residual hearing, and lipreading*, J Acoust Soc Am. 85(6), pp. 2593-607, PMID 2526169 (June 1989).

A vowel discrimination test using a tactual vocoder was administered and the results were compared to that of an eight-channel cochlear implant. The results suggested that an eight-channel and a 16-channel tactile vocoder provided essentially the same discrimination scores. However, the ability to discriminate synthetic vowels decreased rapidly when less than eight channels were employed. The ability of an eight-channel tactile vocoder is expected to be better than that of the eight-channel cochlear implant because it is supposed that vowel discrimination is degraded by a phenomenon known as "current spreading" in the case of cochlear stimulation. See Ifukube, T., *Discrimination of synthetic vowels by using tactile vocoder and a comparison to that of an eight-channel cochlear implant*, IEEE Trans Biomed Eng., 36(11), pp. 1085-91, PMID 2530151 (November 1989); Goldstein, M., and Proctor, A., Tactile aides for profoundly deaf children, J Acoust Soc Am., 77(1), pp. 258-65, PMID 3156167 (January 1985); and U.S. Pat. No. 4,791,620, filed on Mar. 21, 1986, and entitled Tactile Hearing Aid.

Preliminary evaluation of a multichannel electrotactile speech processor. Performance scores on Central Institute for the Deaf ("CID") everyday sentences, Consonant Nucleus Consonant ("CNC") words, and closed-set vowel and consonant identification were significantly improved when using the electrotactile aid. Performance scores, using the aid without lipreading, were well above chance on consonant and vowel identification and on elements of the Minimal Auditory Capabilities Battery. See Cowan, R., Alcantara, J., Blarney, P., and Clark, G., *Preliminary evaluation of a multichannel electrotactile speech processor*, J Acoust Soc Am., 83(6), pp. 2328-38, PMID 2970485 (June 1988); Boothroyd, A., and Hnatch-Chisolm, T., *Spatial, tactile presentation of voice fundamental frequency as a supplement to lipreading*. J Rehabil Res Dev., 25(3), pp. 51-6, PMID 2970543 (Summer 1988); and Brooks, P., Frost, B., Mason, J., and Gibson, D., *Continuing evaluation of the Queen's University tactile vocoder*, Rehabil Res Dev., 23(1), pp. 119-28, PMID 3958993 (January 1986).

A review of the literature suggests that the failure or limitations of tactile substitution systems are due, not to the inadequacy of the skin's perceptual processing capacity, but to inappropriate displays, ineffective training methods, or insensitive testing techniques. Specifically, displays have been artificial in that they have typically failed to preserve the information relevant to the modality for which they are supposed to substitute. Furthermore, certain false assumptions and misconceptions have been manifest in testing techniques that have not taken into account the way in which perceptual processes normally develop and operate. See Richardson, B., and Frost, B., *Sensory substitution and the design of an artificial ear*, J Psychol., 96(2d Half), pp. 259-85, PMID 886486 (July 1977); and Plant, G., *Tactile perception by the profoundly deaf*, Br J Audiol., 16(4), pp. 233-44, PMID 6897619 (November 1982).

The vibrotactile aid provided very useful information as to speech and non-speech stimuli with the subjects performing best on those tasks where time/intensity cues provided sufficient information to enable identification. See Osberger, M., Maso, M., and Sam, L., *Speech intelligibility of children with cochlear implants, tactile aids, or hearing aides*, J Speech Hear Res., 36(1), pp. 186-203, PMID 8450658 (February 1993).

Current research on the effectiveness of tactile aids for speech perception by hearing-impaired persons suggests that substantial training, lasting over months or years, is necessary for users to achieve maximal benefits from a tactile device. A number of studies have demonstrated the usefulness of training programs that include an analytic component, such as phoneme training, together with more synthetic tasks such as sentence identification and speech tracking. However, particularly in programs for children, it is desirable to structure training experiences so that easy distinctions are trained first, and more difficult distinctions are approached only later in training. See Weisenberger J. M., *The transmission of phoneme-level information by multichannel tactile speech perception aids*, Ear Hear, 16(4), pp. 392-406, PMID 8549895 (August 1995); and Bernstein, L E., *Lipreading sentences with vibrotactile vocoders*, J Acoust Soc Am., 90(6), pp. 2971-84, PMID 1838561 (December 1991).

Additional information about tactile hearing and/or tactile hearing devices may be found in the following articles: Renier, L. et al., *Multisensory integration of sounds and vibrotactile stimuli in processing streams for "what" and "where,"* J Neurosci., 29(35), pp. 10950-60, PMID 19726653 (Sep. 2, 2009); Burton, H., Sinclair, R., and McLaren, D., *Cortical Network for Vibrotactile Attention*, Hum Brain Mapp., 29(2), pp. 207-21, PMID 17390318 (February 2008); and Weisenberger J M., *The transmission of phoneme-level information by multichannel tactile speech perception aids*, Ear Hear, 16(4), pp. 392-406, PMID 8549895 (August 1995).

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

I claim:

1. A system for imparting comprehension of sonic information, without outer ear, inner ear or middle ear transmission methods, to a user through skin and through a bone of a user's skull, comprising:
   a. a wearable housing having at least one acoustic transducer operable to generate at least one electrical signal in response to detected sound, the wearable housing including
      i. at least one vibrotactile device operable to generate vibration based on the at least one electrical signal, wherein the at least one vibrotactile device is configured to apply the vibration to the user's skin other than through the user's ear;
      ii. an electrotactile device having at least one electrode in communication with the user, wherein the at least one electrode is configured to apply the at least one electrical signal to the user's skin; and
      iii. an ultrasound conversion device operable to receive the at least one electrical signal, modify the at least one electrical signal to a waveform having one or more frequencies within an ultrasound range, and transmit the modified electrical signal wirelessly, and
   b. an implantable device comprising an anchor portion adapted to be at least partially embedded in the bone of the user's skull, the implantable device being configured to wirelessly receive the modified electrical signal, wherein the anchor portion vibrates with an ultrasonic vibration based on sound encoded in the modified electrical signal, and wherein the ultrasonic vibration is adapted to be transferred to the skull.

2. The system of claim 1, further comprising a strap coupled to the wearable housing, wherein the strap is adapted to engage the user's wrist.

3. The system of claim 1, wherein the implantable device further comprises:
   a. an external unit in releasable communication with the anchor portion, wherein the external unit comprises at least one electro-mechanical transducer configured to receive the ultrasonic vibration and apply the ultrasonic vibration to the anchor portion to cause the anchor portion to vibrate.

4. The system of claim 1, wherein the ultrasound conversion device transmits the modified electrical signal wirelessly to the implantable device.

5. The system of claim 4, wherein the implantable device further comprises a receiver configured to receive the modified electrical signal or signals wirelessly.

6. The system of claim 5, wherein the ultrasound range comprises frequencies greater than 20 kHz.

7. The system of claim 5, wherein the ultrasound conversion device is configured to bypass an inner ear and, wherein the ultrasound conversion devices is adapted to transmit the modified electrical signal via bone conduction to the brain.

8. The system of claim 1, wherein the ultrasound conversion device further comprises a transmitter configured to transmit the modified electrical signal wirelessly.

9. The system of claim 1, wherein the at least one acoustic transducer is configured to detect sounds having frequencies with an audible frequency range.

10. The system of claim 1, wherein the at least one acoustic transducer comprises:
    a. a power source;
    b. at least one processor;
    c. a memory drive having executable instructions; and
    d. one or more network ports,
    wherein the at least one acoustic transducer is programmable, wherein the one or more network ports communicate with one or more external devices, wherein the at least one electrical signal is received by the at least one processor.

11. The system of claim 10, wherein the housing is a watch having a display, wherein the display is a communication interface.

12. The system of claim 10, wherein the housing is incorporated into an accessory selected from the group consisting of a necklace, a belt buckle, a bracelet, a broach, a pin, an arm band, a handbag, a pen, a cellular telephone, a pager, and personal digital assistant.

13. A method for using a vibrio-tactile hearing device comprising the steps of:

a. one or more acoustic transducers detecting sounds in an audible range;
b. the one or more acoustic transducers encoding electrical signals based on the sound;
c. sending the electrical signals to at least one vibration producing device, at least one electrode, and an ultrasound conversion device;
d. the at least one vibrotactile device generating vibrations based on the sounds detected;
e. the at least one vibration producing device applying the vibrations to a user's skin from a housing mounted on the user such that nerves in the skin other than through the user's ear, detect the vibrations;
f. the at least one electrode applying the electrical signals to the user's skin such that nerves in the skin detect the electrical signals;
g. the ultrasound conversion device converting the electrical signals to ultrasonic waves having frequencies;
h. wirelessly transmitting the ultrasonic waves to an implanted device having an anchor portion implanted in a bone of the user's skull;
i. the implanted device receiving the ultrasonic waves; the anchor portion vibrating based on the ultrasonic waves; and
j. applying the vibrations of the anchor portion to the bone of the user's skull such that the bone conducts the vibration to the user's brain's hearing centers for detection thereby,
   wherein the steps of applying the vibrations to the user's skin, applying the electrical signals to the user's skin, and the anchor portion vibrating occur simultaneously.

\* \* \* \* \*